United States Patent

Heckert et al.

[11] 4,006,176
[45] Feb. 1, 1977

[54] ORGANOSILANE COMPOUNDS

[75] Inventors: David C. Heckert, Oxford; David M. Watt, Jr., Cincinnati, both of Ohio

[73] Assignee: The Procter & Gamble Company, Cincinnati, Ohio

[22] Filed: Apr. 22, 1975

[21] Appl. No.: 570,538

[52] U.S. Cl. .................. 260/448.2 N; 260/448.8 R; 252/89 R; 252/541; 428/543

[51] Int. Cl.$^2$ ................ C07F 7/10; C07F 7/18

[58] Field of Search ............ 260/448.8 R, 448.2 N

[56] References Cited

UNITED STATES PATENTS

| | | | |
|---|---|---|---|
| 2,972,598 | 2/1961 | Morehouse | 260/448.8 R X |
| 3,389,160 | 6/1968 | Reid | 260/448.2 N |
| 3,471,541 | 10/1969 | Morehouse | 260/448.2 N X |
| 3,557,178 | 1/1971 | Gölitz et al. | 260/448.8 R |
| 3,580,920 | 5/1971 | Culpepper | 260/448.8 R X |
| 3,624,120 | 11/1971 | Yetter | 260/448.2 N |
| 3,658,867 | 4/1972 | Prokai | 260/448.2 N |
| 3,661,963 | 5/1972 | Pepe et al. | 260/448.2 N |
| 3,817,739 | 6/1974 | Abbott et al. | 260/448.8 R X |
| 3,836,559 | 9/1974 | Prokai | 260/448.2 N |
| 3,898,257 | 8/1975 | Gregory | 260/448.8 R |

Primary Examiner—Paul F. Shaver
Attorney, Agent, or Firm—C. R. Wilson; R. B. Aylor; T. H. O'Flaherty

[57] ABSTRACT

Novel compounds of formula

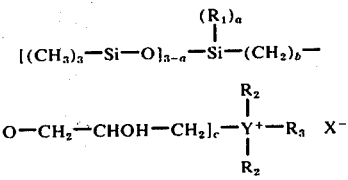

or siloxane oligomers thereof, wherein $a$ is 0 to 2; $R_1$ is an alkyl group containing 1 to 18 carbon atoms; $b$ is 1 to 3; $c$ is 0 or 1; at least one $R_2$ is a carboxy-substituted alkyl group containing 1 to 4 carbon atoms, $$(C_xH_{2x}O)_m Z$$

wherein $x$ is 2 to 4, $m$ is 1 to 20, Z is hydrogen, an alkyl group containing 1 to 18 carbon atoms or an acyl group containing 1 to 4 carbon atoms, or oxygen provided only one $R_2$ is oxygen, and provided $R_2$ is not oxygen when $c$ is 0, while the other $R_2$ is an alkyl, aryl or arylalkyl group containing 1 to 12 carbon atoms; $R_3$ is an alkyl, aryl or arylalkyl group containing 1 to 22 carbon atoms; X is halide; and Y is nitrogen, phosphorus, or sulfur are disclosed. The novel compounds are useful for inclusion in a detergent composition for imparting soil release benefits to metallic and vitreous surfaces washed or rinsed therewith.

11 Claims, No Drawings

ORGANOSILANE COMPOUNDS

BACKGROUND OF THE INVENTION

This invention relates to novel organosilane compounds.

Various quaternized substituted organosilane compounds are known. For example, British Pat. No. 686,068 discloses compounds having the general formula

$(R_3SiCH_2)_aNR^1_bH_{4-a-b}Y$ where R is an alkyl, monocyclic aryl hydrocarbon or alkoxy radical, $R^1$ is an alkyl, alicyclic hydrocarbon or monocyclic aryl hydrocarbon radical or hydroxy alkyl radical, $a$ is 1 or 2, $b$ is 0 to 3 with $a+b$ being not greater than 4. British Pat. No. 1,164,581 discloses compounds of the general formula

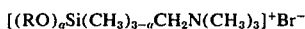

$[(RO)_aSi(CH_3)_{3-a}CH_2N(CH_3)_3]^+Br^-$ wherein R is an alkyl radical containing 1 to 6 carbon atoms or a phenyl radical and $a$ is 1 or 2. U.S. Pat. No. 3,730,701 discloses compounds of the formula

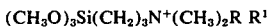

$(CH_3O)_3Si(CH_2)_3N^+(CH_3)_2R\ R^1$ where R is an alkyl group having 11 to 22 carbon atoms and $R^1$ is halide. These compounds are said to be useful as intermediates in the formation of organosilicon resins, catalysts and emulsifying agents (British Pat. No. 686,068), interfacial active agents and as modifiers for organopolysiloxane resins and oils (British Pat. No. 1,164,581) and for the control of algae (U.S. Pat. No. 3,730,701).

British Pat. No. 882,067 discloses compounds of formula

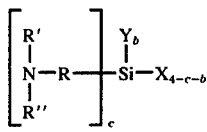

$$\begin{bmatrix} R' \\ | \\ N-R \\ | \\ R'' \end{bmatrix}_c \begin{matrix} Y_b \\ | \\ -Si-X_{4-c-b} \end{matrix}$$

wherein R is a substituted or unsubstituted alkyl group, R' and R'' are hydrogen, or organic radicals, preferably alkyl, aminoalkyl, cyanoalkyl, hydroxyalkyl, carboalkoxyalkyl, carboxyalkyl or aryl radicals, or the monovalent grouping

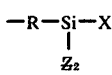

$$\begin{matrix} -R-Si-X \\ | \\ Z_2 \end{matrix}$$

X is an alkoxy radical or the oxygen atom of a siloxylidyne radical $\equiv Si - O -$, or R' and R'' together with the nitrogen atom may form a heterocyclic ring, Y is a hydroxy, alkoxy, alkyl or aryl radical, Z is an alkoxy, alkyl, or aryl radical, $c$ is 1 or 2, $b$ is 0 to 2, and $c+b$ is not more than 3.

Quaternized organosilanes containing trimethylsiloxy radicals attached to the silicon atom are disclosed in U.S. Pat. Nos. 3,389,160, 3,624,120, and 3,658,867. Organosilanes of formula

$R_2N(O)C_aH_{2a}SiZ_3$ where R is a monovalent hydrocarbon group, $a$ is at least 2 and Z is a monovalent hydrocarbon group, an alkoxy, aryloxy group, hydroxy group, a siloxy group or a $R_2N(O)C_aH_{2a}$ - group are disclosed in U.S. Pat. No. 2,955,127.

It has now been found that the novel compounds as hereindescribed are useful as an additive to a detergent composition. Commonly assigned copending Patent Applications "Organosilane-Containing Detergent Composition" and "Organosilane-Containing Anionic Detergent Compositions", both by Heckert and Watt, filed of even date Ser. No. 570,534, filed Apr. 22, 1975 and Ser. No. 570,533, filed Apr. 22, 1975, respectively disclose detergent compositions containing a class of organosilanes. When metallic or vitreous surfaces are washed with a detergent composition containing the organosilane, a thin polymeric coating of the organosilane is deposited upon the washed or rinsed surfaces. The polymerized coating imparts a soil release benefit to the surface, thereby making the surface easier to clean in subsequent washings.

It is an object of this invention to produce novel organosilane compounds.

It is another object of this invention to produce organosilane compounds having utility in a detergent composition.

These and other objects will become apparent from the description to follow.

As used herein all percentages and ratios are by weight unless otherwise indicated.

SUMMARY OF THE INVENTION

An organosilane having the formula

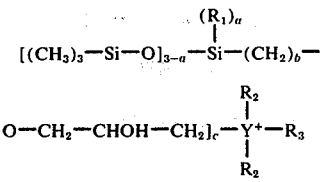

$$[(CH_3)_3-Si-O]_{3-a}-\overset{(R_1)_a}{\underset{|}{Si}}-(CH_2)_b-$$

$$[O-CH_2-CHOH-CH_2]_c-\overset{R_2}{\underset{R_2}{\overset{|}{Y^+}}}-R_3\ X^-$$

or siloxane oligomers thereof, wherein $a$ is 0 to 2; $R_1$ is an alkyl group containing 1 to 18 carbon atoms; $b$ is 1 to 3; at least one $R_2$ is a carboxy-substituted alkyl group containing 1 to 4 carbon atoms,

$(C_xH_{2x}O)_mZ$ wherein $x$ is 2 to 4, $m$ is 1 to 20, Z is hydrogen, an alkyl group containing 1 to 18 carbon atoms or an acyl group containing 1 to 4 carbon atoms, or oxygen provided only one $R_2$ is oxygen and provided $R_2$ is not oxygen when $c$ is 0, while the other $R_2$, if any, is an alkyl, aryl or arylalkyl group containing 1 to 12 carbon atoms; $R_3$ is an alkyl, aryl or arylalkyl group containing 1 to 22 carbon atoms; X is halide; and Y is nitrogen, phosphorus, or sulfur.

DETAILED DESCRIPTION OF THE INVENTION

This invention relates to organosilane compounds having the formula

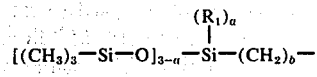

$$[(CH_3)_3-Si-O]_{3-a}-\overset{(R_1)_a}{\underset{|}{Si}}-(CH_2)_b-$$

-continued

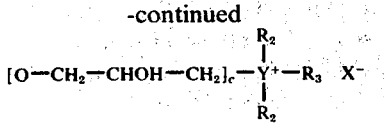

or siloxane oligomers thereof wherein $a$, $R_1$, $b$, $R_2$, $R_3$, $c$, Y and X are as defined immediately above. Preferably X is chloride or bromide, $a$ is 0 or 1, $c$ is 1, $R_2$ is a carboxy-substituted alkyl group and $R_3$ is an alkyl, aryl or arylalkyl group containing 6 to 12 carbon atoms.

It should be understood that $R_2$ in the above formula and formulas to follow may be the same or different. It should be further understood that when Y is sulfur, there will be only one $R_2$. The 1 to 4 carbon atoms in the carboxy-substituted alkyl group is inclusive of the carboxyl group. When one $R_3$ is oxygen or, under basic conditions, the anion of a carboxylic acid substituted alkyl, the counter ion $X^-$ is not extant.

Compounds of the formula

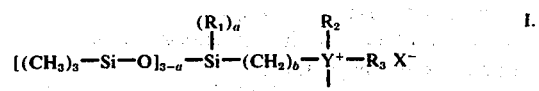    I.

wherein $a$ is 1, $b$ is 3, $R_2$ is a carboxy-substituted alkyl group, and $R_1$, $R_3$, Y and X are defined as above are prepared by the following route:

dihaloalkylsilane may be dissolved in an inert solvent, preferably hexane or pentane. (See W. Noll, "Chemistry and Technology of Silanes", Academic Press, New York, 1968, page 81 for the alcoholysis of halosilanes.) One equivalent of the gamma-halopropyldialkoxylalkylsilane is reacted with one equivalent of the carboxyl-containing tertiary amine, tertiary phosphine, or dialkylsulfide to produce the organosilane. An inert solvent, preferably of high dielectric constant, may be used. The reaction is carried out at temperatures of from 5° to 200° C. and a time of 2 to 20 hours for the reaction of the halopropyldialkoxyalkylsilane. The resultant product is reacted with trimethylchlorosilane at an elevated temperature, e.g. 50° to 200° C. to obtain the desired organosilane.

The starting reactant is commercially available when $R_1$ is $CH_3$. When $R_1$ is $C_2H_5$ or greater, the compound is prepared by reacting a silane with an appropriate olefin. Thus, $$X_2\,SiH_2$$

is reacted with a $C_2$ to $C_{18}$ olefin to obtain the desired starting reactant.

When $a$ is 2, a halodialkylsilane is used as the starting reactant. The subsequent reaction steps are the same as discussed above.

Carboxy-substituted tertiary amines, tertiary phosphines, and dialkylsulfides are produced by reacting

| | | |
|---|---|---|
| $X_2R_1Si\,H\;+\;CH_2{=}CHCH_2X\;\longrightarrow$ | | $X_2R_1Si(CH_2)_3X$ |
| (dihaloalkylsilane)    (allyl halide) | | (gamma-halopropyldihaloalkylsilane) |
| $X_2R_1Si(CH_2)_3X\;+\;2ROH\;\longrightarrow$ | | $(RO)_2R_1Si(CH_2)_3X\;+\;2HX$ |
| (alcohol) | | (gamma-halopropyldialkoxyalkylsilane) |
| $2R_1Si(CH_2)_3X\;+\;(R_2)_{1\;or\;2}YR_3\;\longrightarrow$ | |  |
| (tertiary amine, tertiary phosphine, or dialkylsulfide) | | (gamma-trialkylammoniopropyldialkoxyalkylsilane halide, gamma-trialkylphosphoniopropyldialkoxy-alkylsilane halide, or gamma-dialkylsulfoniopropyldialkoxyalkylsilane halide) |
| 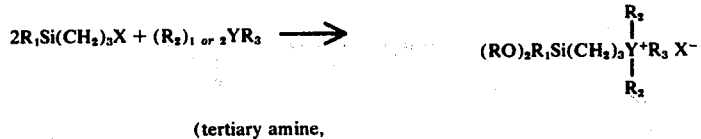 $+\;(CH_3)_3SiX\;\longrightarrow$ | | 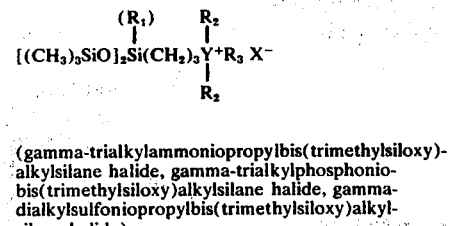 |
| (trimethylchlorosilane) | | (gamma-trialkylammoniopropylbis(trimethylsiloxy)-alkylsilane halide, gamma-trialkylphosphonio-bis(trimethylsiloxy)alkylsilane halide, gamma-dialkylsulfoniopropylbis(trimethylsiloxy)alkyl-silane halide) |

The dihaloalkylsilane (where the halogen is chlorine or bromine) is reacted with the allyl halide at about 100° C. for from 4 to 10 hours in the presence of a catalyst, e.g., chloroplatinic acid or platinum. The resultant gamma-halopropyldihaloalkylsilane is reacted with a lower alcohol to produce the gamma-halopropyldialkoxyalkylsilane. At least two equivalents of alcohol per equivalent of halopropyldihaloalkylosilane are added slowly to the silane. The gamma-halopropyl- $R_2YHR_3$ or $HYR_3$ (where Y is sulfur)

with $X(CH_2)_{1-3}COOH$ in the presence of base at elevated temperatures, e.g. 50° to 150° C.

The compounds of Formula I when at least one $R_2$ is $(C_xH_{2x}O)_mZ$ with x, m and Z as defined above are produced in the manner given above except for the penultimate reaction step. Thus, gamma-halopropyldialkoxysilane is reacted with a tertiary amine, tertiary phosphine, or dialkylsulfide where at least one substituent is $(C_xH_{2x}O)_mZ$ The reaction takes place at a temperature of 50° to 200° C. and a time of from 2 to 10 hours.

When b is 2 in Formula I, a dihalovinylsilane of formula $X_3SiCH=CH_2$ (which is commercially available) is reacted with hydrogen bromide in the presence of peroxide and light to produce a beta-haloethyldihaloalkylsilane. This compound is reacted with an alcohol and thereafter with an appropriate amine, phosphine, or sulfide in the manner discussed above for the preparation of the compounds of Formula I when b is 3.

When b is 1 in Formula I, the starting reactant is a dihaloalkylmethylsilane of formula $X_2R_1SiCH_3$.

This silane is reacted with chlorine or, preferably a half mole of bromine and a half mole of chlorine in the presence of light (such as provided by an ordinary tungsten or fluorescent lamp). The resultant alpha-halomethyldihaloalkylsilane is reacted with an alcohol and thereafter an appropriate amine, phosphine or sulfide in the manner discussed above with the compounds of Formula I when b is 3.

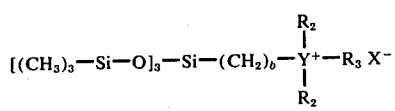

When a is 0, a tris-(trimethylsiloxy)silane is used as the starting reactant. Commercially available trihalosilanes and trimethylsilanes are used to produce the starting reactant. Subsequent reaction steps and conditions as discussed in the preparation of compounds of Formula I are used to produce the desired compound of Formula II.

Examples of compounds of Formulas I and II are:

$[(CH_3)_3SiO]_2CH_3(CH_2)_3N^+(CH_2COOH)_2C_6H_5$ Cl⁻
$[(CH_3)_3SiO]_3SiCH_2N^+(C_2H_4OH)(CH_3)(C_{12}H_{25})$ Cl⁻
$[(CH_3)_3SiO]_3SiCH_2N^+[(C_2H_4O)_{14}H]_2CH_3$ Cl⁻
$[(CH_3)_3SiO]_2CH_3SiCH_2N^+[(C_3H_6O)CH_3](CH_3)_2$ Br⁻
$[(CH_3)_3SiO]_3SiCH_2N^+[(C_2H_4O)_4COCH_3]_2CH_3$ Cl⁻
$[(CH_3)_3SiO]_3SiCH_2P^+(C_2H_4COOH)(C_6H_{13})_2$ Cl⁻
$[(CH_3)_3SiO]_2CH_3Si(CH_2)_2P^+(C_4H_8OH)(CH_3)C_{10}H_{21}$ Cl⁻
$[(CH_3)_3SiO]_3Si(CH_2)_3P^+[(C_2H_4O)_8H]_2C_6H_{13}$ Cl⁻
$[(CH_3)_3SiO]_3SiCH_2P^+[(C_3H_6O)_2C_7H_{15}](C_4H_9)_2$ Br⁻
$[(CH_3)_3SiO]_3Si(CH_2)_2S^+(C_2H_4COOH)C_{12}H_{25}$ Br⁻
$[(CH_3)_3SiO]_3Si(CH_2)_3S^+(C_3H_6OH)C_6H_4CH_3$ Br⁻
$[(CH_3)_3SiO]_3SiCH_2S^+[(C_2H_4O)_{20}H]CH_3$ Br⁻
$[(CH_3)_3SiO]_3Si(CH_2)_3S^+[(C_2H_4O)C_{14}H_{29}]C_2H_5$ Cl⁻

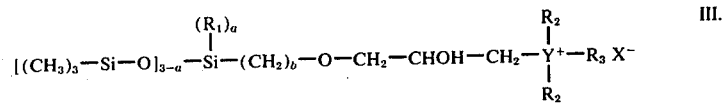

The compounds of Formula III are prepared by initially reacting (when a is 0 and b is 3) trihalosilane with an alcohol (ROH) at 0° to 50° C for 1 to 10 hours to produce a trialkoxysilane. This silane is then reacted with an allylglycidylether.

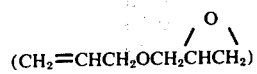

in the presence of 0.01% to 0.1% chloroplatinic acid or platinum at 100° C for 2 to 10 hours. The resultant product

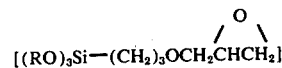

is reacted with a tertiary amine, tertiary phosphine, or dialkylsulfide in the presence of an acid in an inert solvent at 60° to 100° C for 1 to 10 hours. The resultant product is reacted with trimethylchlorosilane at 50° to 200° C to obtain the organosilane of Formula III. The amine, phosphine and sulfide contains at least one carboxy-substituted alkyl group, oxygen or a $(C_xH_{2x}O)_mZ$ group as defined above. The other substituents on the amine, phosphine or sulfide may be an alkyl, aryl or arylalkyl group. When $R_2$ is oxygen, a dialkyl amine, dialkyl phosphine or alkylthiol is reacted with the epoxysilane at 50° to 200° C for from 4 to 10 hours and then with base to produce an intermediate tertiary amine, phosphine, or dialkyl sulfide. These intermediates are then reacted with $H_2O_2$ at 20° to 100° C or preferably $O_3$ in an inert solvent at −80° to 20° C to yield the organosilane.

When a is 1 or 2, the preparation of the compounds is essentially the same except for the use of an alkyl substituted silane as the starting reactant.

When b is 2 in Formula III, a trihalovinylsilane of formula $X_3SiCH=CH_2$ (which is commercially available) is reacted with hydrogen bromide in the presence of peroxide or light to produce a beta-haloethyltrihalosilane. This compound is used to prepare the desired organosilane following the remaining reaction steps discussed immediately above.

When b is 1 in Formula III, the starting reactant is a commercially available trihalomethylsilane of formula $X_3SiCH_3$.

This silane is reacted with chlorine or, preferably a half mole of bromine and a half mole of chlorine in the presence of light (such as provided by an ordinary tungsten or fluorescent lamp). The resultant alpha-halomethyltrihalosilane is used to produce the desired organosilane following the reaction steps outlined above when b is 3.

The following compounds are illustrative of the compounds of Formula III.

[(CH$_3$)$_3$SiO]$_2$CH$_3$SiCH$_2$OCH$_2$CHOHCH$_2$N$^+$(C$_2$H$_4$COOH)(C$_4$H$_9$)$_2$ Cl$^-$

[(CH$_3$)$_3$SiO]$_3$Si(CH$_2$)$_3$OCH$_2$CHOHCH$_2$N$^+$(C$_2$H$_4$OH)$_2$C$_8$H$_{17}$ Cl$^-$

[(CH$_3$)$_3$SiO]$_3$SiCH$_2$OCH$_2$CHOHCH$_2$N$^{+}$(O)$^-$(C$_2$H$_5$)C$_6$H$_4$C$_2$H$_5$

[(CH$_3$)$_3$SiO]$_3$Si(CH$_2$)$_2$OCH$_2$CHOHCH$_2$N$^+$[(C$_2$H$_4$O)$_{10}$H]$_2$CH$_3$ Cl$^-$

[(CH$_3$)$_3$SiO]$_2$C$_2$H$_5$SiCH$_2$OCH$_2$CHOHCH$_2$N$^+$[(C$_2$H$_4$O)$_8$C$_4$H$_9$](CH$_3$)$_2$ Br$^-$

[(CH$_3$)$_3$SiO]$_3$SiCH$_2$OCH$_2$CHOHCH$_2$N$^+$[(C$_3$H$_6$O)$_2$COCH$_3$]$_2$CH$_3$ Br$^-$

[(CH$_3$)$_3$SiO]$_3$Si(CH$_2$)$_2$OCH$_2$CHOHCH$_2$P$^+$(C$_3$H$_6$COOH)$_2$C$_6$H$_5$ Cl$^-$

[(CH$_3$)$_3$SiO]$_2$CH$_3$SiCH$_2$OCH$_2$CHOHCH$_2$P$^+$(C$_2$H$_4$OH)(CH$_3$)C$_8$H$_{17}$ Cl$^-$

[(CH$_3$)$_3$SiO]$_3$Si(CH$_2$)$_3$OCH$_2$CHOHCH$_2$P$^{+}$(O)$^-$(CH$_3$)C$_{10}$H$_{21}$

[(CH$_3$)$_5$SiO]$_3$Si(CH$_2$)$_2$OCH$_2$CHOHCH$_2$P$^+$[(C$_2$H$_4$O)$_2$H]$_2$C$_{10}$H$_{21}$ Br$^-$

[(CH$_3$)$_3$SiO]$_3$SiCH$_2$OCH$_2$CHOHCH$_2$P$^+$[(C$_3$H$_6$O)$_8$C$_2$H$_5$](C$_4$H$_9$)$_2$ Cl$^-$

[(CH$_3$)$_3$SiO]$_2$C$_{12}$H$_{21}$SiCH$_2$OCH$_2$CHOHCH$_2$S$^+$(C$_3$H$_6$COOH)C$_{10}$H$_{21}$ Cl$^-$

[(CH$_3$)$_3$SiO]$_3$SiCH$_2$OCH$_2$CHOHCH$_2$S$^+$(C$_4$H$_8$OH)C$_8$H$_{17}$ Br$^-$

[(CH$_3$)$_3$SiO]$_3$Si(CH$_2$)$_2$OCH$_2$CHOHCH$_2$S$^{+-}$(O)$^-$C$_{16}$H$_{33}$

[(CH$_3$)$_3$SiO]$_3$SiCH$_2$OCH$_2$CHOHCH$_2$S$^+$[(C$_2$H$_4$O)$_6$H]C$_6$H$_4$CH$_3$ Cl$^-$

[(CH$_3$)$_3$SiO]$_3$SiCH$_2$CCH$_2$CHOHCH$_2$S$^+$[(C$_4$H$_8$O)$_{12}$CH$_3$]C$_8$H$_{17}$ Cl$^-$

Siloxane oligomers of the organosilanes are formed from the monomers by the controlled addition of from 1 to 100 equivalents of water, preferably in an inert solvent such as alcohol, tetrahydrofuran, etc. As used herein, "oligomers" is used to mean a degree of polymerization of from 2 to 100, preferably 2 to 20. A higher degree of polymerization adversely affects the ability of the compound to bond itself to a metallic or vitreous surface as discussed below and is for this reason avoided. Examples of siloxane oligomers having varying degrees of polymerization are readily visualized from the above examples of organosilane monomers.

The above organosilanes are useful when used in a detergent composition at a level of organosilane to water-soluble organic detergent of from 2:1 to 1:10,000. When metallic or vitreous surfaces are washed or rinsed with a detergent composition containing the above described organosilane, a soil release benefit is imparted to the surface. It is theorized that the positively charged organosilane is attracted to the negatively charged surface. The silicon atom in the organosilane can then form a bond with the surface. The presence of the positive charge on the organosilane is necessary to allow the bonding to take place from a dilute solution as is normally encountered with detergent compositions and within a reasonable time period. The terminal alkyl groups attached to the positively charged atom provides the soil release benefits. It is believed that the organosilane compound polymerizes on the surface to form a thin coating of the polymer. The coating is responsible for imparting the soil release benefits to the surface. That is, a hard surface having on it the polymeric coating will be soiled; however, the soil is not tenaciously bound to the surface by virtue of the coating and for this reason is easily washed away.

The following examples illustrate this invention.

EXAMPLE I

[(CH$_3$)$_3$SiO]$_3$Si(CH$_2$)$_3$N$^+$(CH$_2$C-H$_2$OCOCH$_3$)$_2$C$_{12}$H$_{25}$ Cl$^-$

Gamma-chloropropyltrichlorosilane (21.1 g., 0.1 mole) is dissolved in 200 ml. of dry ether and an ether slurry of (33.6g, 0.3 mole) sodium trimethylsilanoate, (CH$_3$)$_3$SiONa, is added in small portions. The mixture is allowed to stand for 12 hours and is then refluxed for an additional 3 hours. Filtration of the sodium chloride and removal of the ether from the filtrate leaves gamma-chloropropyltris-trimethylsiloxysilane.

The gamma-chloropropyltristrimethylsiloxysilane (0.1 mole), dodecyldiethanolaminediacetate (0.1 mole), and acetonitrile (100 ml.) are heated to 120° C. for 12 hours in a glass-lined autoclave to yield the desired product.

EXAMPLE II

[(CH$_3$)$_3$SiO]$_2$(CH$_3$)Si(CH$_2$)$_3$OCH$_2$-CHOHCH$_2$N$^+$(CH$_3$)(CH$_2$COO$^-$)CH$_2$C$_6$H$_5$

Methyldichlorosilane (230g., 2 moles) and diallylether (294g., 3 moles) are heated in an autoclave to 100° C. for 12 hours with 0.01 moles of H$_2$Pt Cl$_6$.6H$_2$O.

After 6 hours the product is distilled yielding

Cl$_2$Si(CH$_3$)(CH$_2$)$_3$OCH$_2$CH=CH$_2$.

One mole of this product is added slowly to a slurry of 2.2 moles of sodium trimethylsilanoate in hexane. After stirring for 24 hours, 20 ml. of H$_2$O is added, the lower layer is separated, and the hexane solution is dried over MgSO$_4$. Distillation of the hexane solution yields $$[(CH_3)_3SiO]_2\underset{\underset{CH_3}{|}}{Si}(CH_2)_3OCH_2CH=CH_2.$$

To one-half mole of this product in 500 ml. of hexane is added, portionwise, 0.65 moles of m-chloroperbenzoic acid (85% active). After stirring at 25° C. overnight, the solution is filtered and the hexane is stripped off. Short path distillation of the residue yields the epoxide $$[(CH_3)_3SiO]_2\underset{\underset{CH_3}{|}}{Si}(CH_2)_3OCH_2\overset{O}{\overset{/\ \backslash}{CHCH_2}}.$$

To the above epoxide (100.8g., 0.3 mole) in 100 ml. of dry acetonitrile is added 36.3g. (0.3 mole) of methylbenzylamine and a trace of formic acid. The mixture is stirred for 6 hours and then refluxed for 6 hours yielding a solution of

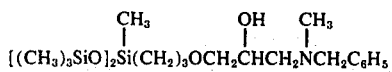

To the above amine (45.7g., 0.1 mole) is added sodium bromoacetate (16.1 gm, 0.1 mole) in 150 ml. of acetonitrile. The mixture is stirred rapidly at room temperature for 12 hours and then warmed to reflux for an additional 3 hours. Removal of the acetonitrile under reduced pressure yields the desired silane.

Corresponding organosilanes wherein there is a phosphorous atom or a sulfur atom in place of the nitrogen atom are produced as above by using methylbenzylphosphine or benzylsulfide in place of the amine compound.

EXAMPLE III

To 0.1 mole (45.7g.) of the tertiary amine,

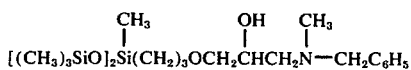

in 150 ml. of dry acetonitrile is added 13.9g. (0.1 mole) of beta-methoxyethylbromide. After stirring for 12 hours at 25° C., the mixture is heated to reflux for an additional 3 hours. Removal of the solvent under reduced pressure, yields the desired quaternary ammonium salt.

EXAMPLE IV

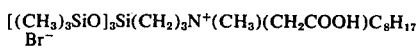

A slurry of 336 grams (3 moles) of sodium trimethylsilylate in one liter of ether is added portionwise to a rapidly stirred solution of 212 grams (1 mole) of 3-chloropropyltrichlorosilane in 400 ml. of ether. After addition of the slurry is complete, the mixture is allowed to stir for an additional 12 hours. The resulting product is filtered and the solvent is removed from the filtrate under reduced pressure to yield tris-trimethylsiloxy-3-chloropropylsilane.

To 186.3 grams (0.5 moles) of the tris-trimethylsiloxy-3-chloropropylsilane in 250 gm. of 2-butanone is added 71.5 grams (0.5 moles) of methyloctylamine. The mixture is heated in an autoclave under 200 psi. nitrogen to 130° C. for 18 hours. The 2-butonone is removed from the product by distillation and the residue is added to two liters of hexane. An excess of trimethylamine (anhydrous gas) is added and the mixture is allowed to stir for 16 hours. Filtration to remove the trimethylamine hydrochloride salt, and short path distillation of the filtrate yields tris-trimethylsiloxy-3-octylmethylaminopropylsilane.

To the above amine, is added 250 ml. of acetonitrile and 17.7 grams (0.11 mole) of sodium bromoacetate. The mixture is refluxed for 6 hours, filtered, and the solvent is removed from the filtrate under reduced pressure leaving the zwitterionic silane.

EXAMPLE V

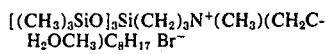

To 47.9 grams (0.1 mole) of the amine

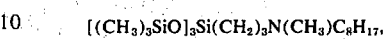

prepared as described in Example IV in 100 ml. of acetonitrile is added 13.9 grams (0.1 mole) of 2-methoxyethyl bromide. The mixture is refluxed for 12 hours and the solvent is evaporated leaving the desired quaternary ammonium salt.

What is claimed is:
1. An organosilane having the formula

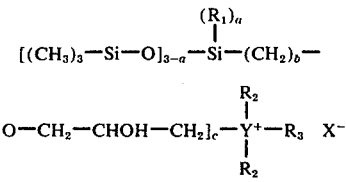

or siloxane oligomers thereof, wherein $a$ is 0 to 2; $R_1$ is an alkyl group containing 1 to 18 carbon atoms; $b$ is 1 to 3; $c$ is 0 to 1; at least one $R_2$ is either (a) a carboxy-substituted alkyl group containing 1 to 4 carbon atoms, (b)

$$(C_xH_{2x}O)_mZ$$

wherein $x$ is 2 to 4, $m$ is 1 to 20, Z is hydrogen, an alkyl group containing 1 to 18 carbon atoms, or an acyl group containing 1 to 4 carbon atoms, or (c) oxygen provided only one $R_2$ is oxygen and provided $R_2$ is not oxygen when $c$ is 0 and that there is no $X^-$ when $R_2$ is oxygen, while the other $R_2$ is an alkyl, aryl or arylalkyl group containing 1 to 12 carbon atoms; $R_3$ is an alkyl, aryl or arylalkyl group containing 1 to 22 carbon atoms; X is halide; and Y is nitrogen, phosphorus or sulfur.

2. The organosilane of claim 1 wherein $c$ is 0.
3. The organosilane of claim 1 wherein $c$ is 1.
4. The organosilane of claim 1 wherein $a$ is 0 or 1.
5. The organosilane of claim 1 wherein the siloxane oligomer has a degree of polymerization of from 2 to 100.
6. The organosilane of claim 5 wherein the degree of polymerization is from 2 to 20.
7. The organosilane of claim 1 wherein the organosilane is a monomer.
8. The organosilane of claim 1 wherein X is chloride or bromide.
9. The organosilane of claim 1 wherein $R_2$ is a carboxy-substituted alkyl group.
10. The organosilane of claim 1 wherein $R_3$ contains 6 to 12 carbon atoms.
11. The organosilane of claim 1 having the formula

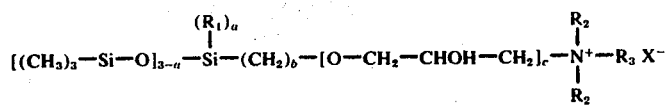

or siloxane oligomers thereof, wherein $a$ is 0 to 2; $R_1$ is an alkyl group containing 1 to 18 carbon atoms; $b$ is 1 to 3; $c$ is 0 or 1; at least one $R_2$ is either (a) a carboxy-substituted alkyl group containing 1 to 4 carbon atoms, (b)

wherein $x$ is 2 to 4, $m$ is 1 to 20, is hydrogen, an alkyl group containing 1 to 18 carbon atoms, or an acyl group containing 1 to 4 carbon atoms or (c) oxygen provided only one $R_2$ is oxygen and provided $R_2$ is not oxygen when $c$ is 0 and that there is no $X^-$ when $R_2$ is oxygen, while the other $R_2$ is an alkyl, aryl or arylalkyl group containing 1 to 12 carbon atoms; $R_3$ is an alkyl, aryl or arylalkyl group containing 1 to 22 carbon atoms; and X is halide.

* * * * *